United States Patent
Tanabe et al.

(10) Patent No.: US 9,867,966 B2
(45) Date of Patent: Jan. 16, 2018

(54) CATHETER ASSEMBLY

(71) Applicants: Terumo Kabushiki Kaisha, Tokyo (JP); Mitsubishi Pencil Company, Limited, Tokyo (JP)

(72) Inventors: Hidenori Tanabe, Yamanashi (JP); Yasunobu Zushi, Yamanashi (JP)

(73) Assignees: TERUMO KABUSHIKI KAISHA, Tokyo (JP); MITSUBISHI PENCIL COMPANY, LIMITED, Tokyo (JP)

( * ) Notice: Subject to any disclaimer, the term of this patent is extended or adjusted under 35 U.S.C. 154(b) by 461 days.

(21) Appl. No.: 14/542,180

(22) Filed: Nov. 14, 2014

(65) Prior Publication Data
US 2015/0080801 A1 Mar. 19, 2015

Related U.S. Application Data

(63) Continuation of application No. PCT/JP2012/062451, filed on May 16, 2012.

(51) Int. Cl.
*A61M 31/00* (2006.01)
*A61M 25/06* (2006.01)
(Continued)

(52) U.S. Cl.
CPC .... *A61M 25/0631* (2013.01); *A61M 25/0606* (2013.01); *A61M 5/3243* (2013.01);
(Continued)

(58) Field of Classification Search
CPC ............... A61M 5/158; A61M 5/3275; A61M 25/0606; A61M 25/0631; A61M 25/0693; A61M 2025/0018
(Continued)

(56) References Cited

U.S. PATENT DOCUMENTS 5,562,631 A * 10/1996 Bogert .............. A61M 25/0631
604/192
9,095,683 B2 * 8/2015 Hall .................. A61M 25/0606
(Continued)

FOREIGN PATENT DOCUMENTS

JP 2005-529717 A 10/2005
JP 4477749 B2 6/2010

OTHER PUBLICATIONS

International Search Report dated Aug. 14, 2012 issued in Application No. PCT/JP2012/062451.

*Primary Examiner* — Edelmira Bosques
(74) *Attorney, Agent, or Firm* — Foley & Lardner LLP

(57) ABSTRACT

A catheter assembly includes: an inner needle; an inner needle hub connected to the inner needle; a catheter through which the inner needle is inserted; a catheter hub connected to a proximal end portion of the catheter; and a protector that covers at least the tip of the inner needle when the inner needle is withdrawn. The protector includes: an inner tube, and an outer tube. The inner tube includes at least one arm that releasably engages with a proximal end of the catheter hub. The catheter assembly is configured such that, when the inner needle is withdrawn, after the tip of the inner needle has been stored in the protector, the outer tube is retracted with respect to the inner tube thereby allowing the at least one arm to be displaced outwardly, whereby engagement between the at least one arm and the catheter hub is released.

19 Claims, 10 Drawing Sheets

(51) Int. Cl.
    *A61M 5/32*     (2006.01)
    *A61M 25/00*    (2006.01)
(52) U.S. Cl.
    CPC ... *A61M 25/0693* (2013.01); *A61M 2005/325* (2013.01); *A61M 2025/0018* (2013.01); *A61M 2205/7536* (2013.01)
(58) Field of Classification Search
    USPC ........................................ 604/167.02, 164.01
    See application file for complete search history.

(56) References Cited

U.S. PATENT DOCUMENTS

2004/0236288 A1     11/2004   Howell et al.
2012/0259292 A1*    10/2012   Koehler ............ A61M 5/16813
                                                              604/256

\* cited by examiner

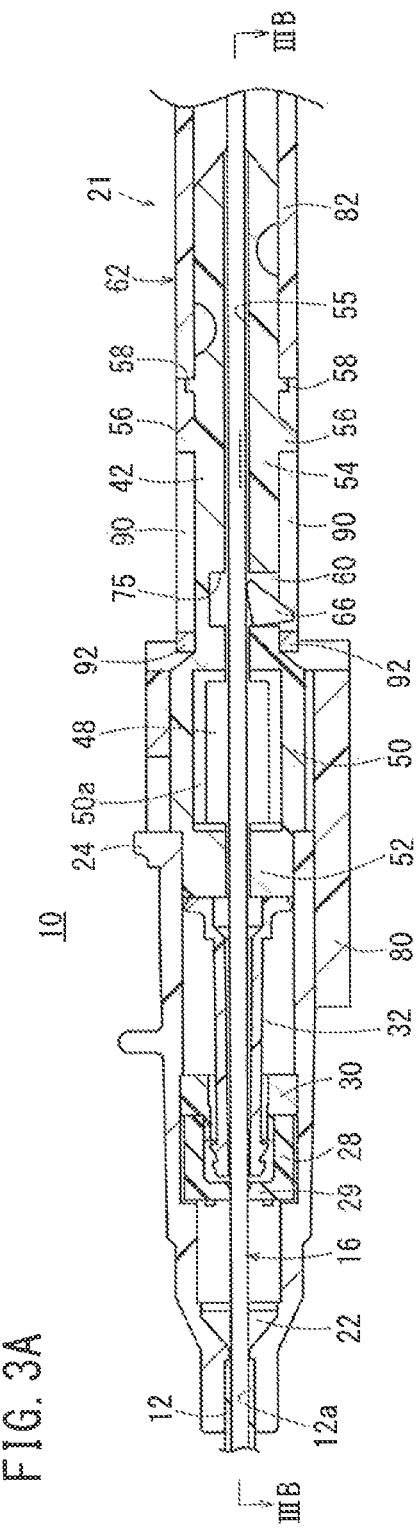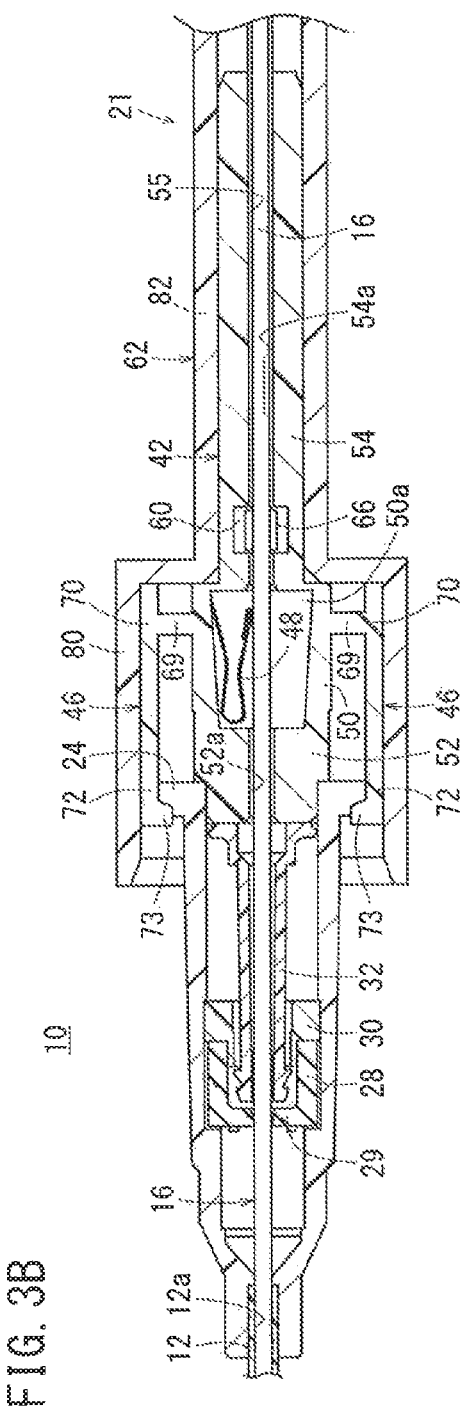

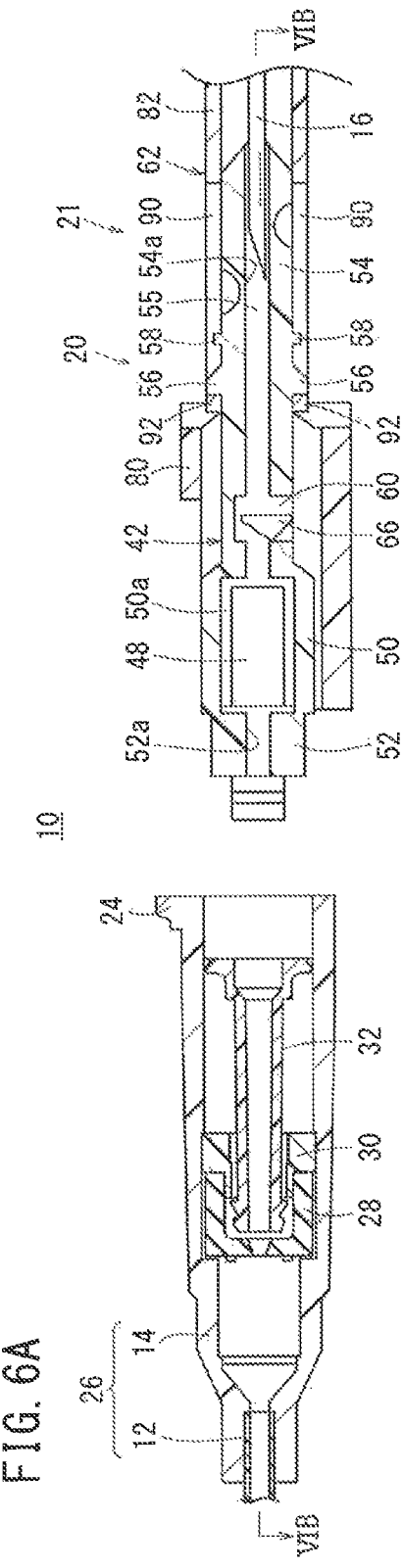
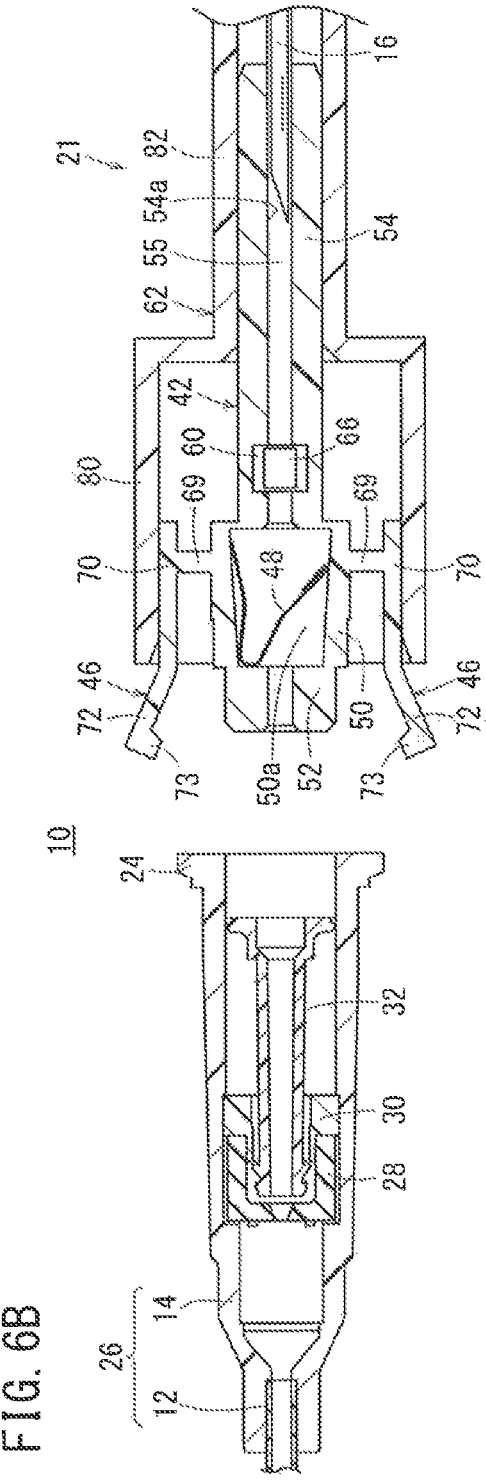
FIG. 6A
FIG. 6B

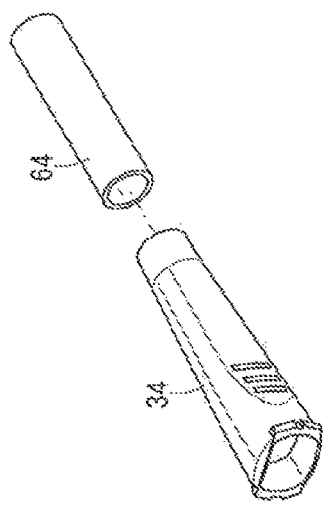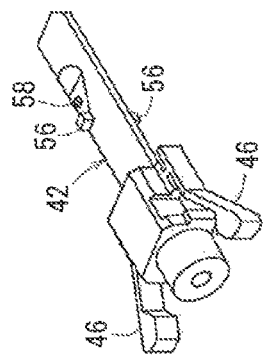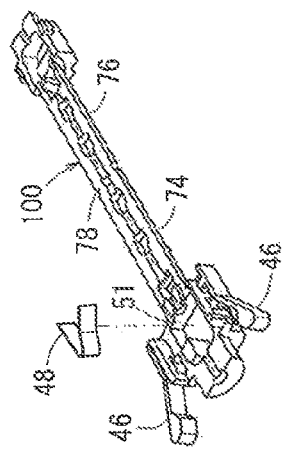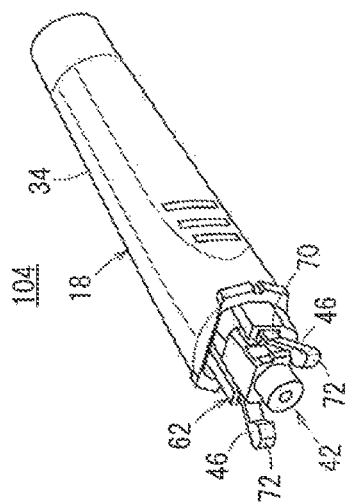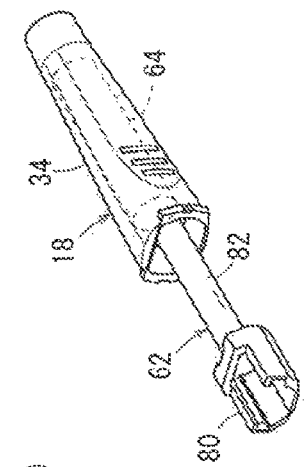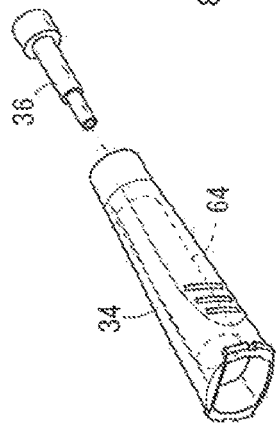

CATHETER ASSEMBLY

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/062451 filed on May 16, 2012, the contents of which is hereby incorporated by reference in its entirety.

BACKGROUND

Technical Field

The present disclosure relates to a catheter assembly that can puncture and remain indwelled in a blood vessel, for example, when performing an infusion on a patient.

Background Art

Conventionally, when an infusion is carried out on a patient, a catheter assembly has been used. This type of catheter assembly is equipped with a hollow outer needle (catheter), an outer needle hub (catheter hub) that is fixed to a proximal end of the outer needle, an inner needle that is inserted into the outer needle and has a sharp tip at a distal end thereof, and an inner needle hub that is fixed to a proximal end of the inner needle. In the event that the catheter assembly is used to perform an infusion on a patient, the outer needle together with the inner needle punctures a blood vessel of the patient, and after puncturing, the inner needle is withdrawn from the outer needle while the outer needle remains in a punctured condition in the patient. Thereafter, a connector, which is provided on a distal end of an infusion tube, is connected to the proximal end of the outer needle hub, and an infusion solution is supplied into the patient's blood vessel through the infusion tube, the outer needle hub, and the outer needle.

Incidentally, during use of this type of catheter assembly, after the inner needle is withdrawn from the outer needle, in order to prevent the inner needle that has a sharp tip from being touched inadvertently by the user, a catheter assembly has been proposed which is equipped with a protector with which the inner needle can be covered following withdrawal from the outer needle (for example, see Japanese Patent No. 4477749).

The safety indwelling needle disclosed in Japanese Patent No. 4477749 makes up part of a catheter assembly. The safety indwelling needle is equipped with a catheter that corresponds to the outer needle and the outer needle hub, an inner needle that is inserted into the catheter, a mounting hub that corresponds to the inner needle hub and is fixed to a proximal end of the inner needle, a slide cover that corresponds to the protector and is mounted extendably on the mounting hub to cover the inner needle in its entirety in an extended state, and a holder that is disposed on a distal end of the slide cover and removably retains the catheter.

The slide cover in the safety indwelling needle is made up from two large and small connecting tubes that are slidably connected, such that when the inner needle is withdrawn from the catheter, accompanying the withdrawing operation, the slide cover is extended maximally. After the slide cover is extended maximally, in order to maintain the slide cover in a non-compressible condition in which the slide cover cannot be returned to its original compressed state, a locking mechanism made up from elastic ribs and locking pawls, etc., is provided on the slide cover. By rotating the holder in a circumferential direction with respect to the catheter, the holder can be placed in engagement with (fixed to) the catheter and released from engagement with respect to the catheter.

Before the slide cover is extended and the total length of the inner needle has been accommodated inside the slide cover, the slide cover can be rotated in a circumferential direction with respect to the catheter, whereby the slide cover can be separated from the catheter. Therefore, in the case that such an operation is made by the user, the inner needle becomes exposed.

Further, for extending the slide cover maximally to bring about the non-compressible condition, it is necessary for the elastic ribs to engage with the locking pawls, which requires a large operating force (tensile force) to a certain degree. Further, after the total length of the inner needle is accommodated inside the slide cover, in order to separate the slide cover from the catheter, it is necessary for the slide cover to be rotated in a circumferential direction with respect to the catheter, and to release the state of engagement between the holder and the catheter. In this case, in order to perform the operation to rotate the slide cover in the circumferential direction, a large operating force is required to a certain degree.

Further, with the aforementioned safety indwelling needle, for withdrawing and separating the inner needle from the catheter in a state in which the inner needle is protected, it is necessary to perform both a pulling-out operation and a rotating operation, and thus the operations tend to be complex.

SUMMARY OF INVENTION

One objective of certain embodiments of the present invention is providing a catheter assembly having a structure in which, after an inner needle has been stored in a protector, the protector and a catheter hub can be separated from one another, and an operation to withdraw the inner needle can be performed with a simple operation and a small operating force.

According to one embodiment of the present invention, a catheter assembly includes an inner needle having a sharp tip at a distal end thereof, an inner needle hub connected to a proximal end portion of the inner needle, a catheter through which the inner needle is inserted, a catheter hub connected to a proximal end portion of the catheter, and a protector that covers at least the tip of the inner needle when the inner needle is withdrawn. The protector has an inner tube that includes an arm that releasably engages with a proximal end of the catheter hub from an outer side thereof, and an outer tube inside which the inner tube is arranged, and which is capable of being displaced relatively in an axial direction with respect to the inner tube. During a withdrawing operation of the inner needle, after the tip of the inner needle has been stored in the protector, the outer tube is retracted with respect to the inner tube and then the arm is displaced outwardly, whereby engagement between the arm and the catheter hub is released.

According to the above structure, engagement between the arm of the inner tube and the catheter hub is released after the inner needle has been stored in the protector in the withdrawing operation of the inner needle, and therefore, the protector and the catheter hub are not separated in a condition in which the inner needle is exposed. Therefore, after using the catheter assembly, the tip can reliably be protected by the protector, and safety can be enhanced during handling of the catheter assembly. Further, because a structure is provided in which engagement between the arm and the catheter hub is released due to the arm being actively opened accompanying relative displacement between the inner tube and the outer tube, the withdrawing operation of the inner needle can be performed by a simple operation and with a small operating force, i.e., merely by pulling the inner needle hub in the direction of the proximal end.

In one aspect, the inner tube may include a hollow inner tube main body, and the arm that is disposed integrally on an outer side of the inner tube main body. The outer tube may include an arm accommodating section in which the arm can be accommodated. Further, in a state in which the arm is arranged in the interior of the arm accommodating section, displacement of the arm in an outward direction may be restricted by the arm accommodating section, and when the outer tube is retracted with respect to the inner tube, the arm may project outwardly from the arm accommodating section, and then the arm may be displaced outwardly by an elastic restoring force.

According to the above structure, in a condition prior to withdrawal of the inner needle, widening of the arm in the outward direction is prevented by the arm accommodating section, whereby engagement between the catheter hub and the protector is reliably maintained. Further, during withdrawal of the inner needle, because the arm is widened outwardly using the elastic restoring force of the arm itself, engagement between the catheter hub and the inner tube is released reliably, and the separation operation can be accomplished smoothly.

In one aspect, the inner tube may have an insertion hole that extends in an axial direction and through which the inner needle is inserted, and a stopper that is disposed so as to face the insertion hole and which is engaged releasably with respect to the outer tube. In a state in which the tip of the inner needle is positioned more toward a distal end side than the stopper, the stopper may be pressed by the inner needle and engaged with the outer tube, whereby the outer tube is prevented from being retracted with respect to the inner tube. In addition, when the tip of the inner needle is moved more toward a proximal end side than the stopper, the stopper may be displaced inwardly and engagement of the stopper with the outer tube may be released, whereby the outer tube becomes capable of being retracted with respect to the inner tube.

According to the above-described structure, by operating the stopper accompanying withdrawal of the inner needle, after the tip of the inner needle has been completely accommodated inside the protector, the outer tube can be moved backward with respect to the inner tube. Therefore, the operation to withdraw the inner needle without the tip becoming exposed can be accomplished more reliably.

In one aspect, the protector may include a positioning unit configured to position the inner tube at a predetermined position with respect to the outer tube, and in a state in which the inner tube is positioned at the predetermined position with respect to the outer tube, the arm may be maintained in an outwardly displaced condition.

According to the above structure, in an assembly process in which the catheter hub and the inner tube are displaced relatively in the axial direction and the catheter hub and the inner tube are engaged with each other, a temporarily assembled condition can be established in which the arm provided on the inner tube is maintained in an open state, whereby there is no possibility for interference between the arm and the catheter hub. Consequently, the connection between the catheter hub and the inner tube can be implemented without causing the arm to buckle.

In one aspect, the positioning unit may include a first protrusion and a second protrusion, which are separated from one another in the axial direction on an outer circumferential portion of the inner tube, and an engagement member disposed on the outer tube and which is capable of engagement with the first protrusion and the second protrusion. By the engagement member being disposed between the first protrusion and the second protrusion, the inner tube may be positioned at the predetermined position with respect to the outer tube.

According to the above structure, by an engagement operation between the engagement member and the first and second protrusions, with a simple structure, during the assembly process, positioning for placing the inner tube and the outer tube in a temporarily assembled condition can securely be carried out.

In one aspect, the first protrusion may be disposed closer to a distal end side in relation to the second protrusion, and when the outer tube is retracted with respect to the inner tube accompanying the withdrawing operation of the inner needle, the first protrusion and the engagement member may come into abutment, so as to restrict further movement of the outer tube with respect to the inner tube.

According to the above structure, during assembly, the first protrusion makes up the positioning unit for maintaining the arm in an open state, while, after the assembly of the product has been completed, the first protrusion functions as a means for restricting the range within which the outer tube can be retracted with respect to the inner tube. Because the first protrusion possesses such multiple functions, the number of protrusions provided on the inner tube can be reduced.

In one aspect, a height at which the second protrusion projects may be lower than a height at which the first protrusion projects.

According to the above structure, when the inner tube is inserted into the outer tube to form the temporarily assembled condition between the inner tube and the outer tube, the second protrusion that is provided on the inner tube can easily overcome the engagement member provided on the outer tube. On the other hand, because it is only necessary to provide an engagement force, which is of a sufficient degree such that the inner tube and the outer tube do not separate from one another during assembly, the second protrusion has no problem in maintaining the temporarily assembled condition.

BRIEF DESCRIPTION OF DRAWINGS

FIG. 3A is an enlarged view of a portion of FIG. 2.

FIG. 3B is a vertical cross sectional view with partial omission taken along line IIIB-IIIB of FIG. 3A.

FIG. 6A is a vertical cross sectional view showing a condition in which a catheter hub and a protector are separated from one another.

FIG. 6B is a vertical cross sectional view taken along line VIB-VIB of FIG. 6A;

FIG. 8A is a first drawing describing an assembly process of a safety member;

FIG. 8B is a second drawing describing the assembly process of the safety member.

FIG. 8C is a third drawing describing the assembly process of the safety member.

FIG. 8D is a fourth drawing describing the assembly process of the safety member.

FIG. 8E is a fifth drawing describing the assembly process of the safety member.

FIG. 8F is a sixth drawing describing the assembly process of the safety member.

DETAILED DESCRIPTION

Hereinafter, a preferred embodiment of a catheter assembly according to the present invention will be described in detail with reference to the accompanying drawings.

Figure 1:
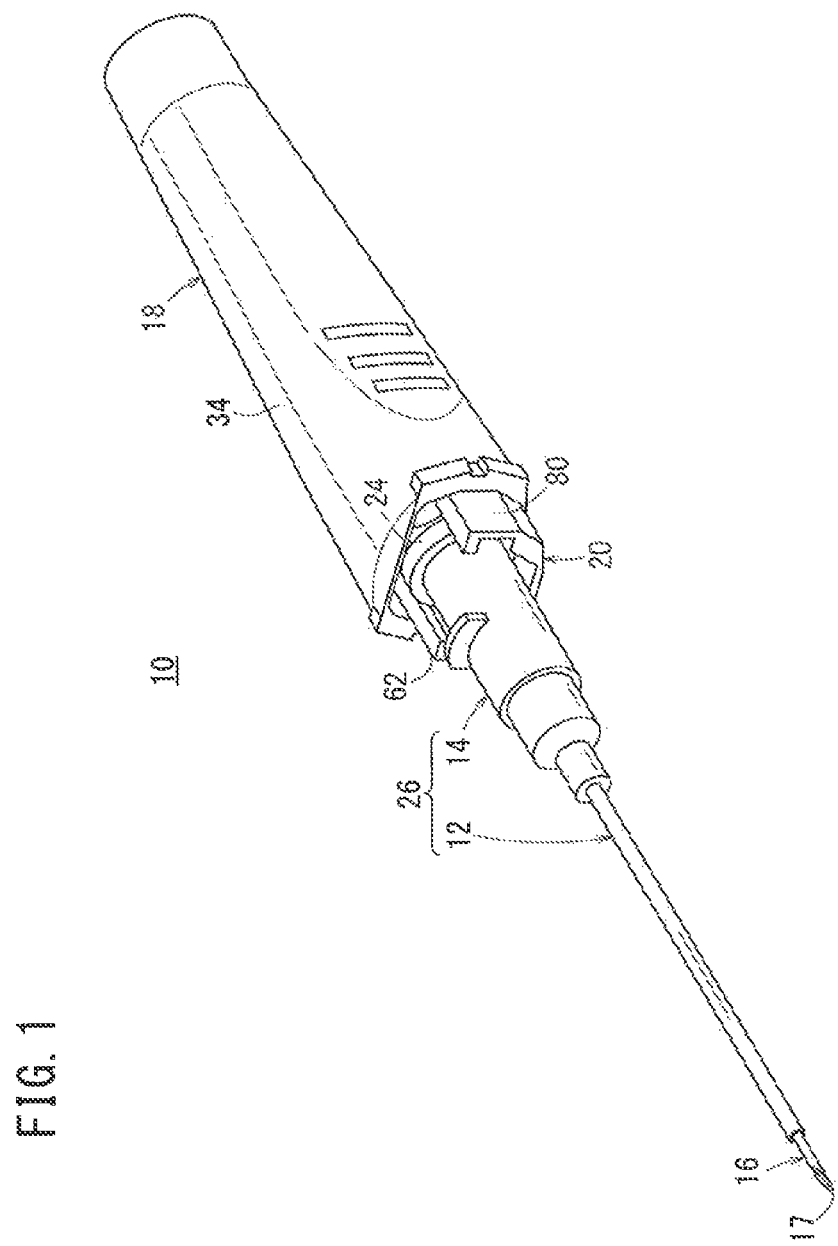
FIG. 1 is a perspective view showing an overall structure of a catheter assembly according to an embodiment of the present invention.
Figure 2:
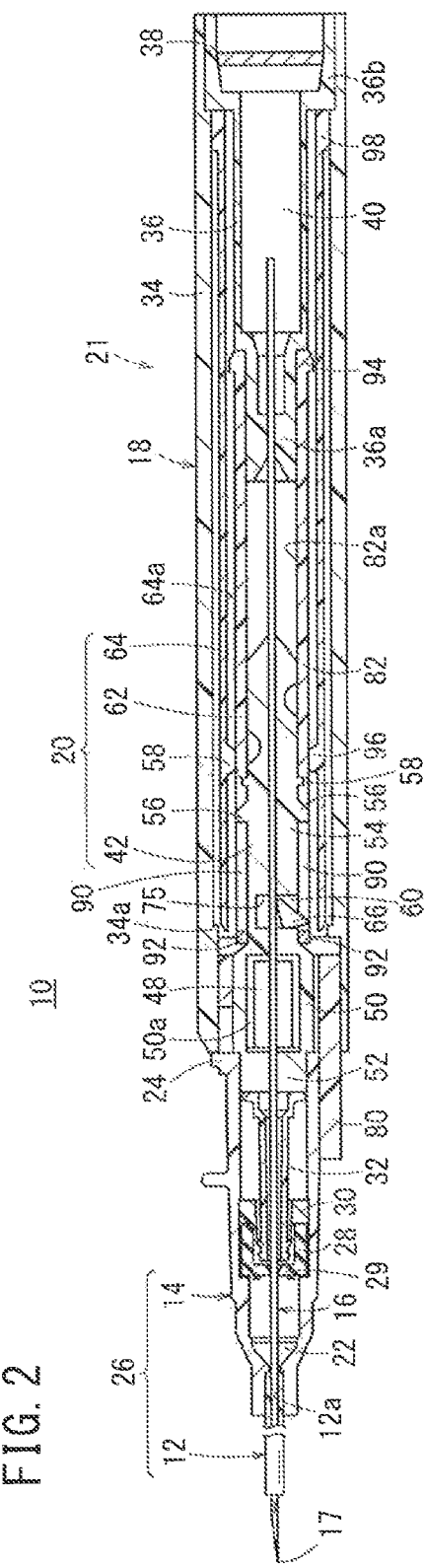
FIG. 2 is a vertical cross sectional view with partial omission of the catheter assembly shown in FIG. 1.

FIG. 1 is a perspective view showing the overall structure of a catheter assembly 10 according to an embodiment of the present invention. FIG. 2 is a vertical cross sectional view with partial omission of the catheter assembly 10.

As shown in FIG. 1, the catheter assembly 10 is equipped with a tubular catheter 12 that functions as an outer needle, a catheter hub 14 that is connected to a proximal end side of the catheter 12, a tubular inner needle 16 having a sharp tip 17 on a distal end thereof and which is capable of being inserted through the interior of the catheter 12, an inner needle hub 18 connected to a proximal end side of the inner needle 16, and a protector 20 that covers the tip 17 of the inner needle 16 when the inner needle 16 is retracted. The catheter assembly 10 can be used in the following manner, which will be described in outline below.

A user (a doctor or nurse, etc.) performs an operation to grip the inner needle hub 18 of the catheter assembly 10, whereby the distal end portion thereof punctures and is inserted into a blood vessel of a patient. In an initial condition prior to use of the catheter assembly 10 (before puncturing the patient), the inner needle 16 is inserted through the catheter 12 in the form of a double tube structure, and the inner needle 16 projects a predetermined length from the distal end of the catheter 12. Hereinbelow, the initial condition of the catheter assembly 10 will be also referred to as a "puncture enabled state". Further, in the initial condition of the catheter assembly 10, the proximal end side of the catheter hub 14 and the distal end side of the inner needle hub 18 are connected through the protector 20.

In the puncture enabled state of the catheter assembly 10, the catheter 12 and the inner needle 16 that make up the double tube structure are inserted together into the blood vessel of the patient. After puncturing the patient, in a condition in which the position of the catheter 12 is maintained, the inner needle hub 18 is retracted in the direction of the proximal end, whereby the protector 20 is made to separate away from the catheter hub 14, whereupon the inner needle 16 that is connected to the inner needle hub 18 is withdrawn integrally therewith, and the inner needle 16 and the inner needle hub 18 are detached from the catheter 12 and the catheter hub 14. As a result, in the catheter assembly 10, a state is brought about in which only the catheter 12 and the catheter hub 14 are left indwelling on the side of the patient.

When the inner needle 16 is withdrawn from the catheter 12, the inner needle 16 becomes accommodated inside the protector 20 due to the protector 20 extending in the distal end direction with respect to the inner needle hub 18. Consequently, exposure of the inner needle 16 to the exterior is prevented. After the inner needle 16 has been withdrawn from the catheter 12, a non-illustrated connector of an infusion tube is connected to the proximal end side of the catheter hub 14, whereby supply of an infusion agent (medicinal solution) is carried out from the infusion tube to the patient.

Below, the structure of the catheter assembly 10 will be described in greater detail.

In the puncture enabled state, the catheter assembly 10 is constituted as a single assembly, in which the double tube structure of the catheter 12 and the inner needle 16, the catheter hub 14, the protector 20, and the inner needle hub 18 are combined and are capable of being handled integrally.

The catheter 12, which is constituted as an outer needle in the catheter assembly 10, is a flexible and narrow diameter tubular member formed with a predetermined length. In the interior of the catheter 12, a lumen 12a is formed to extend and penetrate through the catheter 12 in the axial direction. The inner diameter of the lumen 12a is set to a size that enables the inner needle 16 to be inserted through the lumen 12a.

As the material composing the catheter 12, a resin, particularly, a soft resin material is preferred. In this case, for example, a fluororesin such as polytetrafluoroethylene (PTFE), ethylene-tetrafluoroethylene copolymer (ETFE), perfluoroalkoxy fluororesin (PFA), etc., an olefin resin such as polyethylene, polypropylene, etc., or a mixture thereof, polyurethane, polyester, polyamide, polyether nylon resin, and a mixture of the olefin resin and ethylene-vinyl acetate copolymer may be used. The catheter 12 may be constituted from a transparent resin material, so that all or a portion of the interior is visible.

The catheter hub 14 is connected in a fixed manner to the proximal end of the catheter 12. The catheter hub 14 is formed in a tapered tubular shape. A crimp pin 22 is arranged inside the distal end portion of the catheter hub 14. The distal end portion of the catheter hub 14 and the proximal end portion of the catheter 12 are fixed together mutually in a liquid-tight manner by the crimp pin 22 (see FIG. 2). A flange 24, which projects outwardly and extends in a circumferential direction, is provided on the proximal end of the catheter hub 14. Hereinbelow, the coupling body formed by joining the catheter 12 and the catheter hub 14 will be referred to as a "catheter member 26".

When the catheter assembly 10 is used, the catheter hub 14 is exposed on the patient's skin in a state in which the catheter 12 has pierced into the blood vessel, and is pasted and held in place on the skin by tape or the like. The catheter hub 14 preferably is constituted from a material that is more rigid than the catheter 12. The constituent material of the catheter hub 14 is not limited to any particular material, however, a thermoplastic resin material, such as, for example, polypropylene, polycarbonate, polyamide, polysulfone, polyarylate, methacrylate-butylene-styrene copolymer, etc., preferably can be used.

In the present embodiment, a hemostasis valve 28, a seal member 30, and a plug 32 are arranged in the interior of the catheter hub 14.

The hemostasis valve 28 includes a valve member 29 formed with a slit in a distal end thereof, such that when blood flows into the catheter hub 14 through the lumen of the catheter 12 accompanying puncturing of the blood vessel by the catheter 12, flow of blood to the proximal end side of the catheter hub 14 is prevented.

The seal member 30 is an annular member constituted from a material (e.g., a porous body) that allows flow of gas but blocks flow of liquid through the seal member 30. When the catheter 12 punctures the blood vessel, upon blood flowing to the distal end side in the catheter hub 14 through the catheter 12, air that exists at the distal end side inside the catheter hub 14 passes through the seal member 30 and is discharged to the proximal end inside the catheter hub 14. As a result, the distal end side in the interior of the catheter hub 14 becomes filled with liquid (blood). Consequently, mixing of air into the infusion agent is suppressed.

The plug 32 is formed in a tubular shape and is arranged movably in the axial direction in the interior of the catheter hub 14. In the initial position shown in FIG. 2 (i.e., a position prior to connection of the connector of the infusion tube), the distal end of the plug 32 is positioned on the proximal end side relative to the valve member 29 of the hemostasis valve 28. When the catheter hub 14 and the connector of the infusion tube are connected and the plug 32 is then moved by the connector in the direction of the distal end, the valve member 29 provided in the hemostasis valve 28 is elastically deformed, accompanied by the plug 32 penetrating through the hemostasis valve 28. As a result, a condition is brought about in which the infusion solution can be supplied from the infusion line to the blood vessel through the catheter member 26 (the catheter hub 14 and the catheter 12).

The inner needle 16 is a rigid tubular member that is capable of puncturing the patient's skin. The inner needle is sufficiently longer than the catheter 12, such that in the puncture enabled state (initial condition) of the catheter assembly 10, the tip 17 of the inner needle 16 projects from a distal end opening of the catheter 12. Further, in the puncture enabled state, an intermediate location in the longitudinal direction of the inner needle 16 is inserted through the interior of the catheter hub 14, and the proximal end side thereof is retained inside the inner needle hub 18. As the constituent material of the inner needle 16, a metal material, for example, such as stainless steel, aluminum or aluminum alloy, titanium or titanium alloy, may be used.

The inner needle hub 18 makes up the proximal end side of the catheter assembly 10. The inner needle hub 18 is equipped with a hollow hub main body 34 that constitutes an outer shell that is gripped by the user, and a hollow inner needle retaining member 36 that is fitted into the proximal end side of the hub main body 34. The hub main body 34 is a tubular member formed in a slender elongate shape having a hollow portion of a predetermined volume, and which is formed with an appropriate size (thickness, length) to enable the hub main body 34 to be gripped and operated easily by the user when using the catheter assembly 10. On an inner circumferential portion at a location near the distal end of the hub main body 34, a step 34a is provided, which defines a large diameter on the proximal end side and a small diameter on the distal end side.

The inner needle retaining member 36 is fitted into and fixed to the proximal end side of the hub main body 34, and fixedly retains the proximal end portion of the inner needle 16. The inner needle retaining member 36 is formed in a tubular shape that narrows in diameter stepwise toward the distal end side. The distal end portion, which is smallest in diameter, is constituted as a retaining portion 36a that serves to retain (tightly fix) the proximal end side of the inner needle 16, whereas the proximal end portion, which is largest in diameter, is constituted as an engaging portion 36b that is fitted on the inner surface of the hub main body 34.

A filter 38 is mounted on an inner side of the engaging portion 36b. The filter 38, similar to the seal member 30, is made of a material that blocks the flow of liquid but allows air to pass. The proximal end side of the inner needle retaining member 36 is closed by the filter 38, so as to define a flashback chamber 40 in the interior of the inner needle retaining member 36. The proximal end portion of the inner needle 16 projects into the flashback chamber 40. Therefore, when the inner needle 16 and the catheter 12 puncture the patient, blood flows through the inner needle 16 into the flashback chamber 40. By blood flowing into the flashback chamber 40, the user can determine whether or not the inner needle 16 and the catheter 12 have punctured the patient normally.

When the inner needle 16 is withdrawn from the catheter 12, the protector 20 covers the tip 17 of the inner needle 16 by the inner needle 16 being accommodated in the protector 20. As shown in FIG. 2, the protector 20 includes an inner tube 42 that engages releasably with the proximal end of the catheter hub 14, an outer tube 62 inside which the inner tube 42 is arranged, and which is capable of being displaced relatively with respect to the inner tube 42 within a restricted range in the axial direction, and a joint tube 64 that is inserted inside the outer tube 62 and is capable of sliding axially with respect to the outer tube 62. When a withdrawing operation of the inner needle 16 from the catheter 12 is carried out, the protector 20 is extended to cover the total length of the inner needle 16 (see FIG. 7).

Figure 4A:
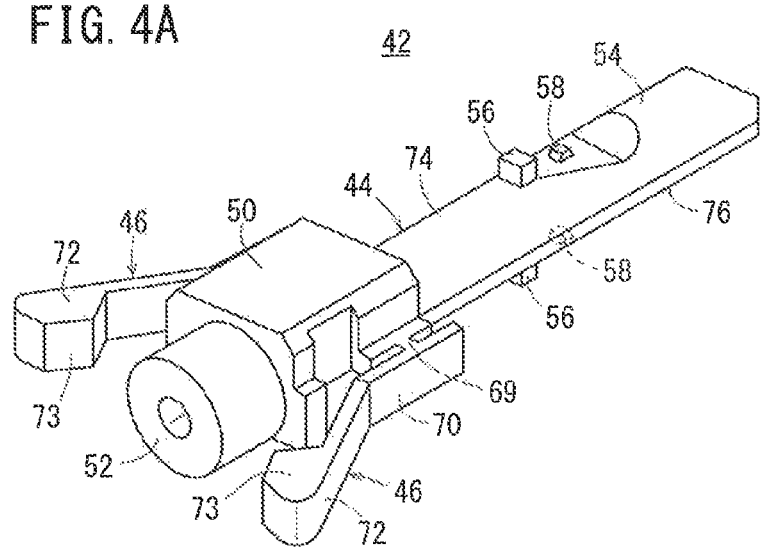
FIG. 4A is a perspective view of an inner tube standing alone.
Figure 4B:
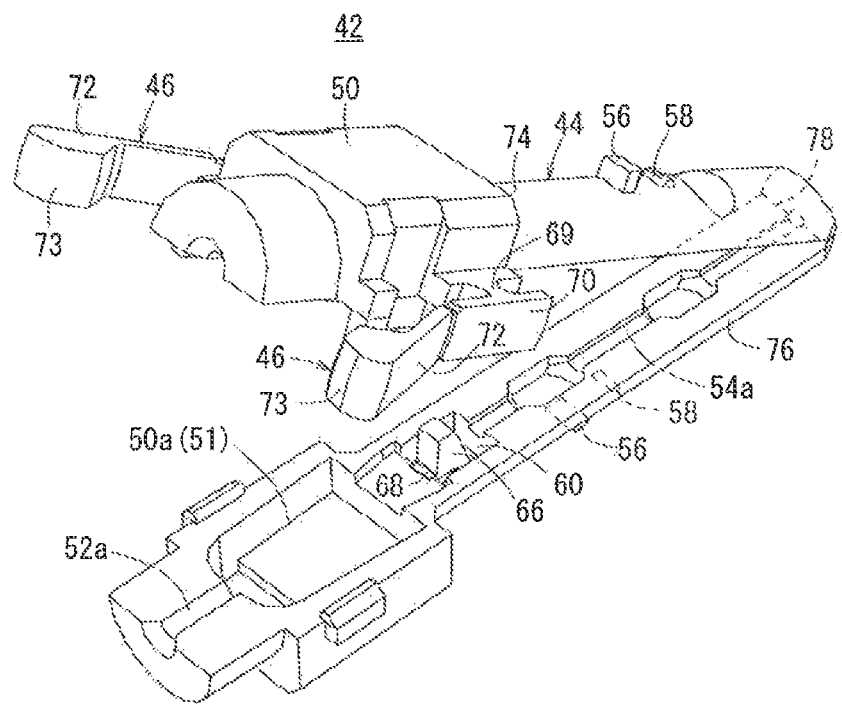
FIG. 4B is a perspective view of the inner tube standing alone during an assembly operation.

FIG. 3A is an enlarged view of a portion of FIG. 2, and FIG. 3B is a vertical cross sectional view with partial omission taken along line IIIB-IIIB of FIG. 3A. In FIGS. 3A and 3B, the inner needle hub 18 and the joint tube 64 are omitted from illustration. FIG. 4A is a perspective view of the inner tube 42 standing alone, and FIG. 4B is a perspective view of the inner tube 42 standing alone during an assembly operation. The inner tube 42 covers the tip 17 of the inner needle 16 accompanying withdrawal of the inner needle 16 from the catheter 12.

As shown in FIGS. 3A to 4A, the inner tube 42 includes a hollow inner tube main body 44 and arms 46 that are disposed integrally on the outer side of the inner tube main body 44. The inner tube main body 44 includes a shutter accommodating section 50 in which a shutter member 48 is accommodated, a distal end tubular section 52 that projects from and is contiguous to a distal end side of the shutter accommodating section 50, and a proximal end tubular section 54 that projects from and is contiguous to the proximal end side of the shutter accommodating section 50. An insertion hole 55, which penetrates in the axial direction and through which the inner needle 16 can be inserted, is disposed in the inner tube main body 44.

A description will be given below concerning the shutter member 48 that is accommodated in the shutter accommodating section 50. As shown in FIG. 3B, the shutter member 48 is an elastic member, which is formed by bending a plate-shaped member into a V-shape. In a condition in which the apex of the shutter member 48 is oriented toward the distal end side of the inner tube 42, the shutter member 48 is disposed in an interior space 50a, which is formed inside the shutter accommodating section 50. The interior space 50a makes up a portion of an insertion hole 55 through which the inner needle 16 can be inserted.

In the initial state of the catheter assembly 10, the inner needle 16 penetrates back and forth through the interior space 50a, and in this state, the shutter member 48 is elastically compressed and deformed due to being pressed from the side surface of the inner needle 16, and is placed in a state of being closed into a smaller shape. As the constituent material of the shutter member 48, for example, a pseudoelastic alloy (including a superelastic alloy) such as a Ni—Ti alloy, a shape memory alloy, stainless steel, a cobalt-based alloy, noble metals such as gold and platinum, a tungsten-based alloy, carbon-based materials, etc. may be used.

As shown in FIGS. 3A and 3B, the distal end tubular section 52 is of a cylindrical shape, and in a state in which the catheter hub 14 and the inner tube 42 are engaged (connected), the distal end tubular section 52 is fitted into the proximal end of the catheter hub 14. A hollow portion 52a of the distal end tubular section 52 makes up another portion of the insertion hole 55 through which the inner needle 16 can be inserted.

The proximal end tubular section 54 is a tubular body, which is longer in comparison to the distal end tubular section 52. A hollow portion 54a of the proximal end tubular section 54 makes up another portion of the insertion hole 55 through which the inner needle 16 can be inserted. The hollow portion 52a of the distal end tubular section 52 and the hollow portion 54a of the proximal end tubular section 54 are disposed on the same straight line, and communicate with one another through the interior space 50a.

As shown in FIGS. 3A and 4A, first protrusions 56 and second protrusions 58, which are separated from one another in the axial direction, are disposed on an outer circumferential portion of the proximal end tubular section 54. In the present embodiment, the first protrusions 56 are provided as a pair, at mutually opposing locations (at locations shifted 180° in phase) on the outer circumferential portion of the proximal end tubular section 54. Similarly, the second protrusions 58 are provided as a pair, at mutually opposing locations on the outer circumferential portion of the proximal end tubular section 54. The height at which the second protrusions 58 project is lower than the height at which the first protrusions 56 project.

As shown in FIGS. 3A and 3B, at a location near the distal end of the proximal end tubular section 54, a side hole 60 is provided that communicates between the interior and the exterior of the proximal end tubular section 54. Further, as shown in FIG. 3A, in the interior of the proximal end tubular section 54, a groove 75 is disposed at a location facing the side hole 60. As shown in FIG. 2, a stopper 66, which is arranged so as to face the insertion hole 55 (more specifically, the hollow portion 54a provided in the proximal end tubular section 54) and which is arranged to engage releasably with respect to the outer tube 62, is disposed in the inner tube 42.

The stopper 66 is capable of being displaced between a first position (see FIG. 3B), in which the stopper 66 can engage with the outer tube 62 that is arranged on the outer side of the inner tube 42, and a second position (see FIG. 6A) that is located more inwardly of the inner tube 42 than the first position, and in which engagement with the outer tube 62 is released and the stopper 66 enters into the interior of the insertion hole 55. In the present embodiment, the stopper 66 is arranged within the side hole 60, and is formed integrally with the proximal end tubular section 54 through a hinge 68. The hinge 68 is an elastically deformable portion that is interposed between the stopper 66 and the proximal end tubular section 54.

In a state in which the tip 17 of the inner needle 16 is positioned more on the distal end side than the stopper 66, the stopper 66 is pressed outwardly by the inner needle 16, and by engagement with the outer tube 62, retraction of the outer tube 62 with respect to the inner tube 42 is prevented. On the other hand, in a state in which the tip 17 of the inner needle 16 is moved more toward the proximal end side than the stopper 66, the stopper 66 is displaced inwardly and engagement with the outer tube 62 is released, whereby it becomes possible for the outer tube 62 to be retracted with respect to the inner tube 42.

The arms 46 are capable of releasably engaging, from the outside, with the proximal end of the catheter hub 14. In the present embodiment, the arms 46 are provided as a pair on left and right side surfaces of the shutter accommodating section 50. More specifically, as shown in FIGS. 2, 4A and 4B, each of the arms 46 includes a support section 69 that projects outwardly from a left or right side surface of the shutter accommodating section 50, an arm base section 70 connected to an outer end of the support section 69 and which extends in parallel with respect to the axial direction of the inner tube main body 44, and an engaging end section 72, which is formed continuously with the distal end side of the arm base section 70. Proximal ends of the arm base sections 70 project in the proximal end direction from the support sections 69, and therefore the length in the axial direction of the arm base sections 70 can be increased accordingly. Engagement pawls 73, which can engage with the flange of the catheter hub 14, are provided integrally on distal end inner sides of the engaging end sections 72.

As shown in FIG. 4A, in a condition in which no external force is applied and the engaging end sections 72 are in a free state, the engaging end sections 72 are tilted and expanded outwardly in the direction of the distal end, and by elastic deformation of the connection locations between the engaging end sections 72 and the arm base sections 70, the engaging end sections 72 can be displaced in a direction perpendicular to the axis of the inner tube main body 44. Operations of the arms 46 will be described below, at a section in which the relationship between the inner tube 42 and the outer tube 62 is described.

In the present embodiment, the inner tube 42 is formed by bending a single member (inner tube forming part 100 shown in FIG. 8A) in half at an intermediate position in the longitudinal direction thereof. More specifically, as shown in FIG. 4B, the inner tube 42 is constituted from a first part 74 the makes up one side portion (an upper portion as shown in the drawing), and a second part 76 that makes up another side portion (a lower portion as shown in the drawing) with reference to the axis (lumen) thereof, and the inner tube 42 is an integrally molded piece in which the respective proximal ends of the first part 74 and the second part 76 are connected by a hinge 78. The insertion hole 55 is formed between the first part 74 and the second part 76, as a result of the first part 74 and the second part 76 being overlapped in a predetermined positional relation.

With the present embodiment, the first part 74 mainly constitutes the upper side of the inner tube 42, and the second part 76 mainly constitutes the lower side of the inner tube 42. The aforementioned pair of arms 46 is disposed integrally on the first part 74, and the stopper 66 is disposed on the second part 76. The pair of arms 46 may also be provided on the second part 76 that constitutes the lower side part. The stopper 66 may also be provided on the first part 74 that constitutes the upper side part. One of the pair of first protrusions 56 is disposed on the first part 74, whereas the other of the pair of first protrusions 56 is disposed on the second part 76. One of the pair of second protrusions 58 is disposed on the first part 74, whereas the other of the pair of second protrusions 58 is disposed on the second part 76.

Figure 5A:
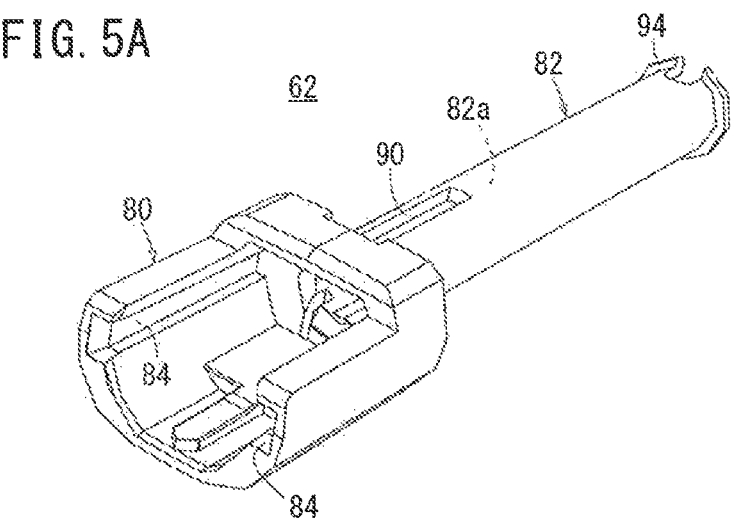
FIG. 5A is a perspective view of an outer tube standing alone as seen from above of a distal end thereof.

As shown in FIGS. 3A and 3B, the outer tube 62 includes an arm accommodating section 80 in which the arms 46 can be accommodated, and a tubular section 82 that projects from the proximal end side of the arm accommodating section 80. FIG. 5A is a perspective view of an outer tube 62 standing alone as seen from above of a distal end thereof, FIG. 5B is a perspective view of the outer tube 62 standing alone as seen from above of a proximal end thereof, and FIG. 5C is a perspective view of the outer tube 62 standing alone as seen from below of the proximal end.

Figure 5B:
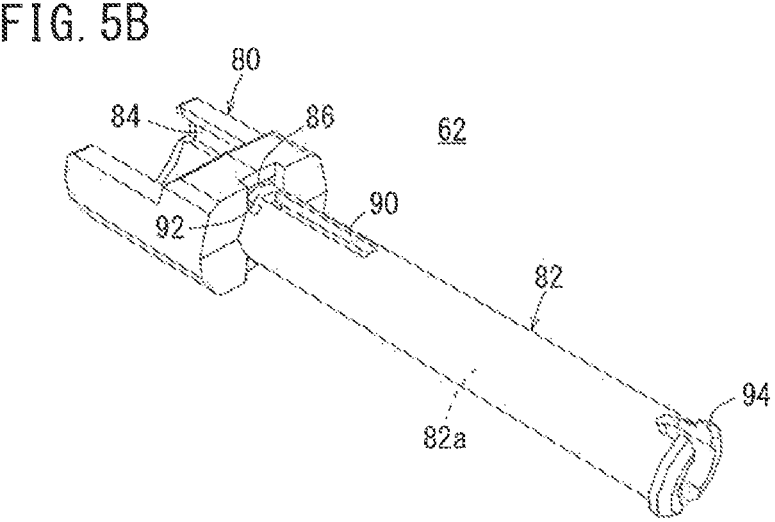
FIG. 5B is a perspective view of the outer tube standing alone as seen from above a proximal end thereof.
Figure 5C:
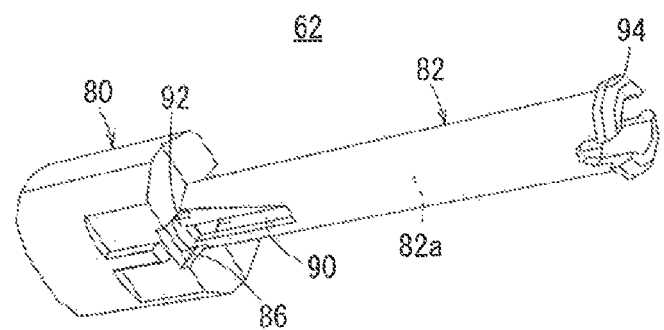
FIG. 5C is a perspective view of the outer tube standing alone as seen from below the proximal end thereof.

As shown in FIGS. 5A to 5C, the arm accommodating section 80 is formed in a box-like shape and opens on the upper portion and the distal end portion thereof. In the puncture enabled state of the catheter assembly 10, the proximal end of the catheter hub 14 and the distal end side of the inner tube 42 (the pair of arms 46 and the shutter accommodating section 50) are arranged in the interior of the arm accommodating section 80. As shown in FIG. 5A, on the inner side surfaces on both left and right sides of the arm accommodating section 80, guide grooves 84 for slidably guiding the arms 46 of the inner tube 42 are formed along the axial direction of the outer tube 62. The guide grooves 84 open respectively on the distal end side of the arm accommodating section 80.

As shown in FIG. 5C, on the upper portion and the lower portion of the proximal end of the arm accommodating section 80, an opening 86 is provided, which penetrates in the axial direction of the outer tube 62. In the tubular section 82 of the outer tube 62, a lumen 82a that communicates with the interior of the arm accommodating section 80 is formed to penetrate in the axial direction. On upper and lower portions at locations near the distal end of the tubular section 82, a pair of elongate slits 90, which penetrate through the inside and outside of the tubular section 82, are disposed along the axial direction of the tubular section 82.

As shown in FIGS. 5B and 5C, at the distal end of the outer tube 62, a pair of engagement members 92 are provided that correspond to the pair of slits 90. The pair of engagement members 92 are disposed to project toward the inside of the opening 86 that is provided on the proximal end of the arm accommodating section 80. The engagement members 92 are capable of being elastically deformed outwardly when pressing forces are applied thereto from the inside. An outer side hook 94, which projects outwardly and extends in a circumferential direction, is provided on the outer side surface of the proximal end of the outer tube 62.

Next, the relationship (state of connection) between the inner tube 42 and the outer tube 62, which are constructed in the foregoing manner, will be described. As shown in FIG. 2, the proximal end tubular section 54 of the inner tube 42 is inserted into the tubular section 82 of the outer tube 62, and the first protrusions 56 and the second protrusions 58 provided on the inner tube 42 are inserted into the pair of slits 90 provided in the outer tube 62. In the puncture enabled state (initial condition) of the catheter assembly 10, because the stopper 66 is inserted into the lower side slit 90 under an outwardly directed pressing action by the inner needle 16 and also engaged with the engagement member 92 provided on the outer tube 62, displacement of the outer tube 62 in the proximal end direction with respect to the inner tube 42 is restricted. Displacement of the outer tube 62 in the distal end direction with respect to the inner tube 42 is restricted by abutment between the rear wall of the arm accommodating section 80 and the proximal end of the shutter accommodating section 50. Further, in this condition, as shown in FIG. 3B, because the arms 46 provided on the inner tube 42 are positioned inside the arm accommodating section 80 of the outer tube 62, widening of the arms 46 is prevented by the inner walls of the arm accommodating section 80 acting against the elastic forces of the arms 46, and the arms 46 remain in a closed state.

On the other hand, accompanying movement of the inner needle 16 more toward the proximal end side than the stopper 66, the stopper 66 is displaced inwardly and engagement between the stopper 66 and the engagement member 92 is released, whereby it becomes possible for the outer tube 62 to be displaced in the proximal end direction with respect to the inner tube 42. Because the length in the axial direction can be increased due to the proximal ends of the arm base sections 70 projecting in the proximal end direction from the support sections 69, in combination with a guiding action by the guide grooves 84, the inner tube 42 and the outer tube 62 can be moved smoothly relative to each other.

FIG. 6A is a vertical cross sectional view showing a condition in which the catheter hub 14 and the protector 20 are separated from one another, and FIG. 6B is a vertical cross sectional view taken along line VIB-VIB of FIG. 6A.

As shown in FIG. 6A, when the outer tube 62 is displaced in the proximal end direction with respect to the inner tube 42, the first protrusions 56 provided on the inner tube 42 come into abutment against the engagement members 92 provided on the outer tube 62, whereby further displacement of the outer tube 62 in the proximal end direction with respect to the inner tube 42 is prevented. Further, in this case, as shown in FIG. 6B, the engaging end sections 72 of the arms 46 project toward the distal end from the arm accommodating section 80, whereby the restriction on widening of the arms 46 by the arm accommodating section 80 is released. As a result, the arms 46 are displaced (widened) outwardly by the elastic restoring forces thereof.

As shown in FIG. 2, the joint tube 64 includes a lumen 64a in which the tubular section 82 of the outer tube 62 can be accommodated, and is assembled in a slidable manner relatively with respect to the outer tube 62. An inner side hook 96, which projects inwardly and extends in a circumferential direction, is provided on the inner side surface of a portion of the joint tube 64 that is positioned near the distal end. The inner side hook 96 is capable of engaging with the outer side hook 94 that is provided on the outer tube 62. An outer side hook 98, which projects outwardly and extends in a circumferential direction, is provided on the outer side surface of the proximal end of the joint tube 64. The outer side hook 98 is capable of engaging with the step 34a that is provided on the inner circumferential portion of the hub main body 34.

The materials constituting the aforementioned respective members (the hub main body 34, the inner needle retaining member 36, the inner tube 42, the outer tube 62, the joint tube 64) of the inner needle hub 18 and the protector 20 are not particularly limited, and for example, may be the same materials as given in the description of the catheter hub 14. In this case, all of these members may be formed from the same material, or may be formed from different materials for each of the members.

The catheter assembly 10 according to the present embodiment is constructed basically as described above. Next, explanations shall be given concerning operations and advantages of the catheter assembly 10.

As shown in FIG. 2, in the initial condition (puncture enabled state) of the catheter assembly 10, the inner needle 16 is inserted into the catheter 12, and the tip 17 projects a predetermined length from the distal end of the catheter 12. In addition, the distal end tubular section 52 of the inner tube 42 is inserted into the proximal end of the catheter hub 14, and the outer tube 62 is moved maximally within the movable range thereof toward the distal end side with respect to the inner tube 42. Further, as shown in FIG. 3B, the pair of arms 46 provided on the inner tube 42 are positioned inside the arm accommodating section 80 of the outer tube 62, whereby the arms 46 are placed in a closed state. The closed pair of arms 46 engages with the flange 24 of the catheter hub 14, whereby separation of the catheter hub 14 from the protector 20 including the inner tube 42 is prevented.

Further, as shown in FIG. 2, in the initial condition (puncture enabled state) of the catheter assembly 10, the tip 17 of the inner needle 16 is positioned more on the distal end side than the stopper 66, and the stopper 66 projects outwardly from the proximal end tubular section 54 of the inner tube 42 and then engages with the engagement member 92 of the outer tube 62, whereby movement of the outer tube 62 in the proximal end direction with respect to the inner tube 42 is prevented. Furthermore, the joint tube 64 is inserted maximally into the inner needle hub 18, and the tubular section 82 of the outer tube 62 is inserted maximally into the joint tube 64. In this state, the arm accommodating section 80 is inserted into the distal end side of the inner needle hub 18. Further, the shutter member 48 is held in an elastically deformed state by the inner needle 16 nearer to one side of the interior space 50a.

In the puncture enabled state, a user (a doctor or nurse, etc.) performs an operation to grip the inner needle hub 18 of the catheter assembly 10, whereby the catheter 12 and the inner needle 16 thereof puncture and are inserted into a blood vessel of a patient. After puncturing, a detachment operation (withdrawing operation of the inner needle 16) is carried out to detach the coupling body (referred to below as an "inner needle unit 21"), which is made up from the inner needle 16, the inner needle hub 18, and the protector 20, from the catheter member 26.

In the detachment operation, in a state in which the position of the catheter member 26 is maintained, the inner needle hub 18 is retracted in the proximal end direction. Upon doing so, the inner needle 16, which is retained by the inner needle retaining member 36 of the inner needle hub 18, starts to be retracted with respect to the catheter 12. On the other hand, a condition (movement stopped state) is maintained, in which the protector 20 cannot be displaced with respect to the catheter member 26, until the inner needle 16 has been retracted by a predetermined amount.

Figure 7:
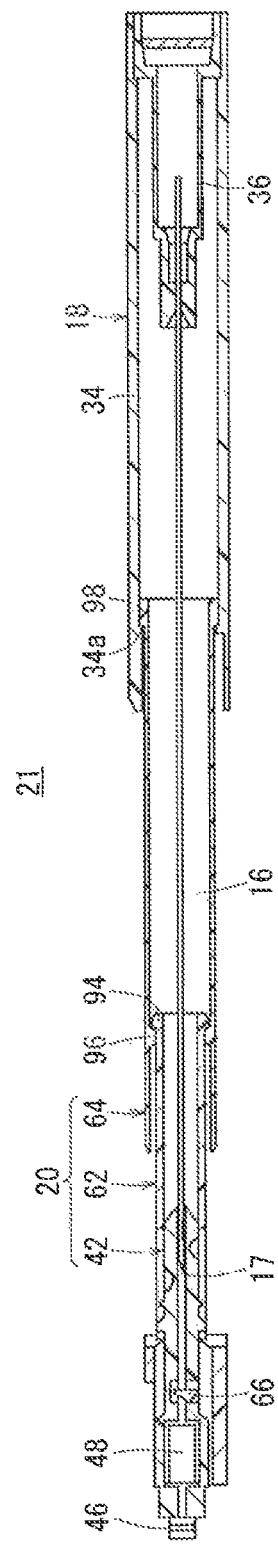
FIG. 7 is a vertical cross sectional view showing a condition in which the catheter hub and the protector are separated from one another and a tip of an inner needle is covered by the protector.

When the inner needle hub 18 is retracted by a predetermined amount, the step 34a (see FIG. 2), which is disposed on the distal end side of the hub main body 34, engages with the outer side hook 98 on the proximal end side of the joint tube 64, and therefore, accompanying retraction of the hub main body 34, the joint tube 64 also is retracted. Upon further retraction of the hub main body 34, the inner side hook 96 on the distal end side of the joint tube 64 engages with the outer side hook 94 on the proximal end side of the tubular section 82. Thus, in this state, a condition is brought about in which the outer tube 62, the joint tube 64, and the inner needle hub 18 are expanded to the maximum extent. Further, in this state, together with the inner needle hub 18 being retracted with respect to the joint tube 64, because by retraction of the joint tube 64 with respect to the outer tube 62, the protector 20 also is expanded, as shown in FIG. 7, the inner needle 16 is covered over its entire length by the inner needle hub 18 and the protector 20.

On the other hand, during the process of retracting the inner needle hub 18 with respect to the catheter member 26, the inner needle 16 also is retracted with respect to the inner tube 42. At this time, when the tip 17 (see FIG. 2) of the inner needle 16 moves more toward the proximal end side than the shutter member 48 that is arranged inside the inner tube 42, the shutter member 48, expansion of which had been restricted as a result of being pressed from the inner needle 16, expands into the interior space 50a by the elastic restoring force thereof (refer to the condition of the shutter member 48 shown in FIG. 6B). As a result, because the passage in which the inner needle 16 can move through the interior space 50a is blocked, the tip 17 of the inner needle 16 is prevented from projecting out again from the distal end of the inner tube 42. Nonetheless, at this time, the arms 46 provided on the inner tube 42 remain closed, and engagement between the inner tube 42 and the catheter hub 14 is maintained.

The inner needle 16 is further retracted within the inner tube 42, and when the tip 17 thereof moves more toward the proximal end side than the stopper 66 that is disposed in the inner tube 42, pressure on the stopper 66 from the inner needle 16 is released, and under the elastic restoring force of the hinge 68, the stopper 66 is displaced inwardly of the inner tube 42 (refer to the condition of the stopper 66 shown in FIG. 6A). Upon the stopper 66 being displaced to the inside of the inner tube 42, because engagement between the stopper 66 and the engagement member 92 disposed on the outer tube 62 is released, the outer tube 62 becomes capable of being displaced in the proximal end direction with respect to the inner tube 42. Therefore, from the condition in which the outer tube 62, the joint tube 64, and the inner needle hub 18 are displaced relatively and expanded maximally in the axial direction, when a movement operation is performed to move the inner needle hub 18 further in the proximal end direction, the outer tube 62 is displaced in the proximal end direction with respect to the inner tube 42.

In addition, along with such displacement, as shown in FIG. 6B, the engaging end sections 72 of the arms 46 project toward the distal end from the arm accommodating section 80, and then the restriction of widening of the arms 46 by the arm accommodating section 80 is released, whereby the arms 46 are actively displaced (widened) outwardly by the elastic restoring forces thereof. As a result, because engagement between the arms 46 provided on the inner tube 42 and the flange 24 provided on the catheter hub 14 is released, accompanying movement of the inner needle hub 18 in the proximal end direction, the inner tube 42 separates from the catheter hub 14. When this is done, the inner needle 16, which is connected to the inner needle hub 18, also is withdrawn from the catheter 12, whereupon the inner needle unit 21 becomes detached from the catheter member 26. As a result, the inner needle unit 21 separates away from the catheter member 26, and among the elements of the catheter assembly 10, only the catheter member 26 itself remains in an indwelling state on the side of the patient.

In a state in which the inner needle unit 21 has been separated from the catheter member 26, the total length of the inner needle 16 is accommodated in the interior of the protector 20 and the inner needle hub 18, and a condition is brought about in which the tip 17 of the inner needle 16 is covered. On the other hand, after the inner needle 16 has been withdrawn from the catheter 12, a non-illustrated connector of an infusion tube is connected to the proximal end side of the catheter hub 14, whereby supply of an infusion agent (medicinal solution) is carried out from the infusion tube to the patient.

With the catheter assembly 10 according to the present embodiment, engagement between the arms 46 of the inner tube 42 and the catheter hub 14 is released after the inner needle 16 has been stored in the protector 20 in the withdrawing operation of the inner needle 16, and therefore, the protector 20 and the catheter hub 14 are not separated in a condition in which the inner needle 16 is exposed. Therefore, after using the catheter assembly 10, the tip 17 can reliably be protected by the protector 20, and safety can be enhanced during handling of the catheter assembly 10.

Further, in the case of the present embodiment, because a structure is provided in which engagement between the arms 46 and the catheter hub 14 is released due to the arms 46 being actively opened accompanying relative displacement between the inner tube 42 and the outer tube 62, the withdrawing operation of the inner needle 16 can be performed by a simple operation and with a small operating force, i.e., simply by pulling the inner needle hub 18 in the direction of the proximal end.

In the case of the present embodiment, in a state in which the arms 46 are arranged inside the arm accommodating section 80, outward displacement of the arms 46 is restricted by the arm accommodating section 80. On the other hand, when the outer tube 62 is retracted with respect to the inner tube 42, accompanying the arms 46 projecting outwardly from the arm accommodating section 80, the arms 46 are displaced outwardly by the elastic restoring forces thereof. According to this structure, in a condition prior to withdrawal of the inner needle 16, widening in the outward direction of the arms 46 is prevented by the arm accommodating section 80, whereby engagement between the catheter hub 14 and the protector 20 is reliably maintained. Further, during withdrawal of the inner needle 16, because the arms 46 are widened outwardly using the elastic restoring forces of the arms 46 themselves, engagement between the catheter hub 14 and the protector 20 is released reliably, and the separation operation can be accomplished smoothly.

With the present embodiment, in a state in which the tip 17 of the inner needle 16 is positioned more on the distal end side than the stopper 66, the stopper 66 is pressed by the inner needle 16 and engages with the outer tube 62, whereby retraction of the outer tube 62 with respect to the inner tube 42 is prevented. On the other hand, when the tip 17 of the inner needle 16 is moved more toward the proximal end side than the stopper 66, the stopper 66 is displaced inwardly and engagement with the outer tube 62 is released, whereby it becomes possible for the outer tube 62 to be retracted with respect to the inner tube 42. According to this structure, by operating the stopper 66 accompanying withdrawal of the inner needle 16, after the tip 17 of the inner needle 16 has been completely accommodated inside the protector 20, the outer tube 62 can be moved backward with respect to the inner tube 42. Therefore, without the tip 17 becoming exposed, the operation to separate the catheter hub 14 and the protector 20 can be accomplished more reliably.

Next, with reference to FIGS. 8A to 10C, the assembly method of the aforementioned catheter assembly 10 will be described. In FIG. 8A, an inner tube forming part 100, which forms the inner tube 42 by being bent, is shown. First, with reference to FIG. 8A, in the inner tube forming part 100, the shutter member 48 is inserted at a location 51 that corresponds to the shutter accommodating section 50 (see FIG. 2), and thereafter, the inner tube forming part 100 is folded in half at the position of the hinge 78 to thereby form the inner tube 42 (see FIG. 8B).

Then, the joint tube 64 is inserted from the proximal end side of the hub main body 34 (see FIG. 8C), followed by the inner needle retaining member 36 being inserted from the proximal end side of the hub main body 34, and the inner needle retaining member 36 is fixed in the hub main body 34 (see FIG. 8D). Next, the outer tube 62 is inserted from the distal end side of the hub main body 34, whereby the outer tube 62 also is inserted into the joint tube 64 which is disposed in the interior of the hub main body 34 (see FIG. 8E). In this case, the proximal end of the outer tube 62 is reduced in diameter along with elastic deformation thereof, whereby the outer side hook 94 (see FIG. 2), which is provided on the outer tube 62, overcomes and moves past the inner side hook 96 provided on the joint tube 64, and the outer tube 62 is inserted into the joint tube 64.

Figure 10A:
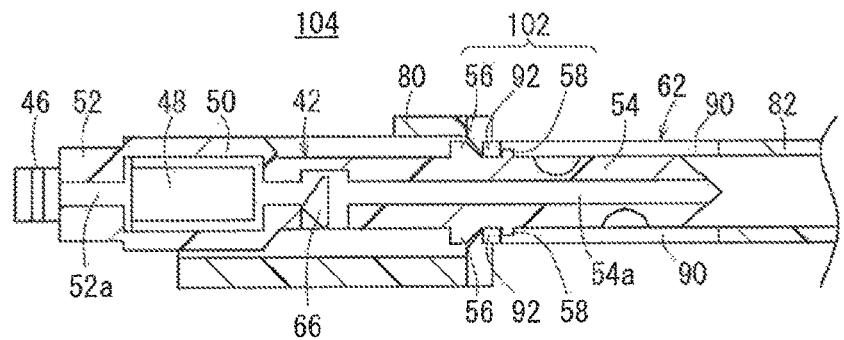
FIG. 10A is a vertical cross sectional view of the safety member in the condition shown in FIG. 8F.

Next, the inner tube 42 is inserted from the distal end side of the outer tube 62, and the inner tube 42 is positioned at a predetermined position with respect to the outer tube 62 to thereby render a temporarily assembled condition (see FIG. 8F). The relationship between the inner tube 42 and the outer tube 62 in the temporarily assembled condition is shown in FIG. 10A. During the process of inserting the inner tube 42 to the predetermined position in the outer tube 62, the engagement members 92 are elastically deformed outwardly, whereby the second protrusions 58 overcome and move past the engagement members 92, and can be moved more toward the proximal end side than the engagement members 92.

As shown in FIG. 10A, in the temporarily assembled condition, by disposing the engagement members 92, which are provided on the outer tube 62, between the first protrusions 56 and the second protrusions 58 that are provided on the inner tube 42, the inner tube 42 is positioned in a predetermined position with respect to the outer tube 62. In this manner, according to the present embodiment, a positioning unit 102 for positioning the inner tube 42 at a predetermined position with respect to the outer tube 62 is constituted by the first protrusions 56 and the second protrusions 58 that are provided on the inner tube 42, and the engagement members 92 that are provided on the outer tube 62.

In the temporarily assembled condition, without the inner tube 42 being inserted maximally with respect to the outer tube 62, the engaging end sections 72 of the arms 46 provided on the inner tube 42 project from the distal end side of the arm accommodating section 80 of the outer tube 62. Thus, a condition in which the engaging end sections 72 are tilted outwardly with respect to the arm base sections 70, i.e., a condition in which the arms 46 are opened, is brought about. Below, for facilitating explanation, the semi-finished product shown in FIGS. 8F and 10A will be referred to as a "safety member 104". In some cases, the safety member 104, which is fabricated in the foregoing manner, can be maintained in this state for a fixed period during transport, storage, or the like, until the inner needle 16 and the catheter member 26 are assembled with the safety member 104 to form the catheter assembly 10.

Figure 10B:
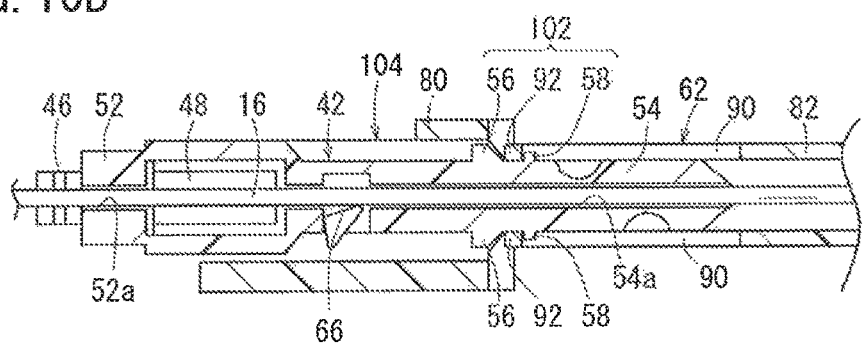
FIG. 10B is a vertical cross sectional view of the safety member and the inner needle in the condition shown in FIG. 9A.

Next, an assembly process for assembling the safety member 104 together with the inner needle 16 and the catheter member 26 will be described. The inner needle 16 is inserted into the catheter member 26, and the inner needle 16 also is inserted into the safety member 104, which is in the temporarily assembled state (see FIG. 9A). As shown in FIG. 10B, when the inner needle 16 is inserted into the inner tube 42, the stopper 66 is pressed by the inner needle 16, whereby the stopper 66 is displaced toward the outer side to bring about a condition in which the stopper 66 projects outwardly from the proximal end tubular section 54.

In this manner, if the inner needle 16 is inserted into the safety member 104 in the temporarily assembled condition, the proximal end of the inner needle 16 becomes firmly fixed to the inner needle retaining member 36. In this case, the proximal end of the inner needle 16 and the inner needle retaining member 36 may be fixed to one another by applying an ultraviolet curable adhesive to a predetermined location of the inner needle retaining member 36, and by irradiating the applied ultraviolet curable adhesive with ultraviolet radiation to harden the same.

In the case of the present embodiment, the hemostasis valve 28, the seal member 30, and the plug 32 (see FIG. 2, etc.) are arranged in the interior of the catheter member 26. However, in accordance with a different embodiment, these elements may be omitted.

Figure 9A:
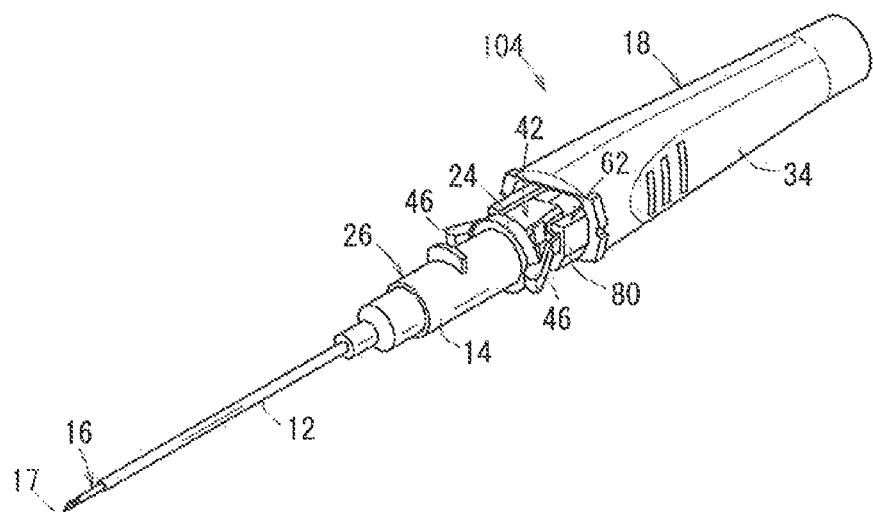
FIG. 9A is a first drawing describing an assembly process of a catheter member and the inner needle together with the safety member.
Figure 9B:
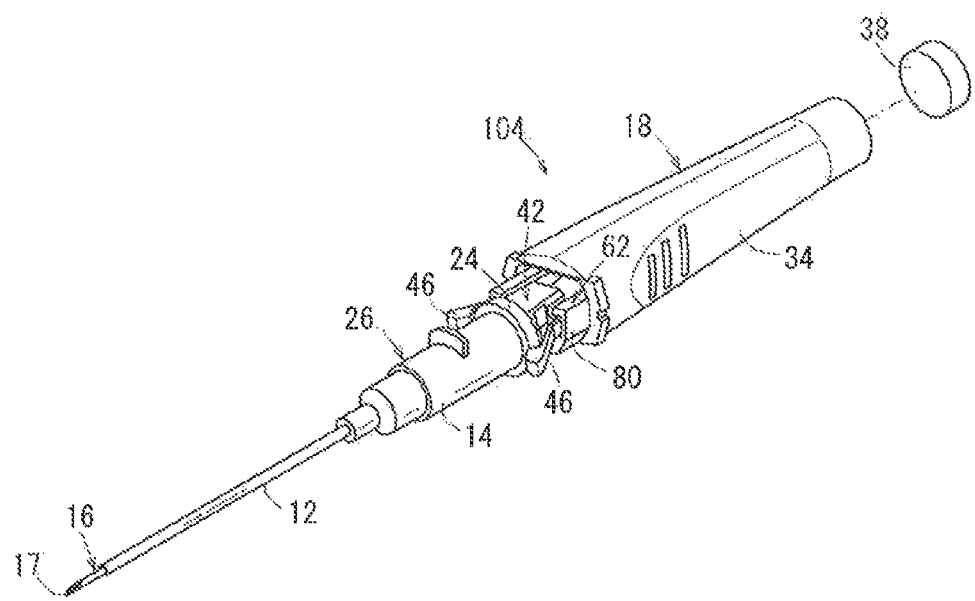
FIG. 9B is a second drawing describing the assembly process of the catheter member and the inner needle together with the safety member.

Next, the filter 38 is fixed to the inside of the proximal end portion (engaging portion) of the inner needle retaining member 36, for example, by welding or an adhesive or the like (see FIG. 9B).

Figure 10C:
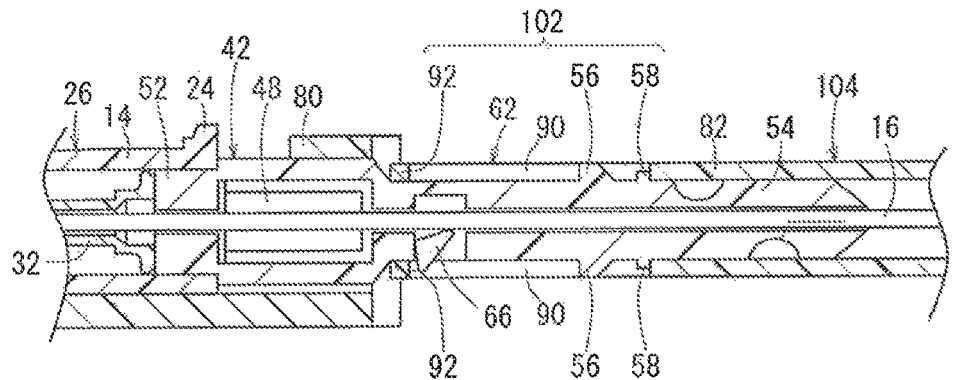
FIG. 10C is a vertical cross sectional view of the catheter assembly in an assembled condition.

Then, as shown in FIG. 10C, by the catheter member 26 being pressed in the proximal end direction with respect to the safety member 104, the inner tube 42 is moved maximally in the proximal end direction with respect to the outer tube 62. In this case, at the time that pressing of the catheter member 26 in the proximal end direction with respect to the safety member 104 is started, because the arms 46 provided on the inner tube 42 are in an open state, when the catheter hub 14 pushes the inner tube 42, the distal ends of the arms 46 do not abut against the proximal end of the catheter hub 14. Therefore, the connection between the catheter hub 14 and the inner tube 42 can be implemented without causing the arms 46 to buckle.

During the process of moving the inner tube 42 in the proximal end direction with respect to the outer tube 62, the arms 46 provided on the inner tube 42 are displaced inwardly accompanying accommodation of the arms 46 in the arm accommodating section 80, and the arms 46 are placed in a closed state. As a result, the engaging end sections 72 of the arms 46 come into engagement with the flange 24 that is provided on the proximal end of the catheter hub 14, and a condition is brought about in which separation between the catheter hub 14 and the inner tube 42 is prevented.

Further, during the process of moving the inner tube 42 in the proximal end direction with respect to the outer tube 62, the stopper 66 that is provided on the inner tube 42 overcomes and moves past the engagement member 92 that is provided on the outer tube 62. In this case, the engagement member 92 is elastically deformed and displaced outwardly, whereby the stopper 66 can overcome the engagement member 92. In addition, at the point in time that the stopper 66 reaches the slit 90, the stopper 66 enters into the slit 90 and comes into engagement with the engagement member 92. Consequently, a condition is created in which relative movement in the axial direction between the inner tube 42 and the outer tube 62 is prevented.

By undergoing the assembly process described above, the catheter assembly 10 having the condition shown in FIGS. 1 and 2 is completed.

As has been described above, with the present embodiment, because the positioning unit 102 is provided on the inner tube 42 and the outer tube 62, in an assembly process in which the catheter hub 14 and the inner tube 42 are displaced relatively in the axial direction and the catheter hub 14 and the inner tube 42 are engaged with each other, the arms 46 provided on the inner tube 42 are maintained in an open state, and therefore there is no possibility for interference between the arms 46 and the catheter hub 14. Consequently, the connection between the catheter hub 14 and the inner tube 42 can be implemented without causing the arms 46 to buckle.

In the case of the present embodiment, the positioning unit 102 is constituted from the first protrusions 56 and the second protrusions 58 that are provided on the inner tube 42, and the engagement members 92 that are provided on the outer tube 62 (see FIG. 10A). According to such a structure, by the engagement operation between the engagement members 92 and the first protrusions 56 and the second protrusions 58, with a simple structure, during the assembly process, positioning for placing the inner tube 42 and the outer tube 62 in a temporarily assembled condition can securely be carried out.

In the case of the present embodiment, during use of the catheter assembly 10, when the outer tube 62 is retracted with respect to the inner tube 42 accompanying the withdrawing operation of the inner needle 16, the first protrusions 56 and the engagement members 92 come into abutment, so as to restrict further movement of the outer tube 62 with respect to the inner tube 42 (see FIG. 6A). In this manner, during assembly, the first protrusions 56 make up the positioning unit 102 for maintaining the arms 46 in an open state, while, after the assembly of the product has been completed (when the product is used), the first protrusions 56 function as means for restricting the range within which the outer tube 62 can be retracted with respect to the inner tube 42. Because the first protrusions 56 possess such multiple functions, the number of protrusions provided on the inner tube 42 can be reduced.

In the case of the present embodiment, the height at which the second protrusions 58 project is lower than the height at which the first protrusions 56 project. According to this structure, when the inner tube 42 is inserted into the outer tube 62 to form the temporarily assembled condition between the inner tube 42 and the outer tube 62, the second protrusions 58 that are provided on the inner tube 42 can easily overcome the engagement members 92 provided on the outer tube 62. On the other hand, because it is only necessary to provide an engagement force, which is of a sufficient degree such that the inner tube 42 and the outer tube 62 do not separate from one another during assembly, the second protrusions 58 have no problem in maintaining the temporarily assembled condition.

Although a preferred embodiment of the present invention has been described, the present invention is not limited to the above-described embodiment. Various modifications can be adopted therein without departing from the scope of the invention.

What is claimed is:

1. A catheter assembly comprising:
an inner needle having a sharp tip at a distal end thereof;
an inner needle hub connected to a proximal end portion of the inner needle;
a catheter through which the inner needle is inserted;
a catheter hub connected to a proximal end portion of the catheter; and
a protector that covers at least the tip of the inner needle when the inner needle is withdrawn,
wherein the protector comprises:
an inner tube, and
an outer tube in which the inner tube is arranged, and which is configured to be displaced in an axial direction relative to the inner tube,
wherein the inner tube comprises:
at least one arm that releasably engages with a proximal end of the catheter hub from an outer side of the catheter hub,
an insertion hole that extends in an axial direction and in which the inner needle is disposed, and
a stopper disposed so as to face the insertion hole, and which is configured to be releasably engaged with the outer tube,
wherein the catheter assembly is configured such that, when the inner needle is withdrawn, after the tip of the inner needle has been stored in the protector, the outer tube is retracted with respect to the inner tube thereby allowing the at least one arm to be displaced outwardly, whereby engagement between the at least one arm and the catheter hub is released.

2. The catheter assembly according to claim 1,
wherein the inner tube further comprises a hollow inner tube main body,
wherein the at least one arm is disposed integrally on an outer side of the inner tube main body, and
wherein the outer tube comprises an arm accommodating section in which the at least one arm is accommodated.

3. The catheter assembly according to claim 2,
wherein the catheter assembly is configured such that, in a state in which the at least one arm is arranged in an interior of the arm accommodating section, displacement of the at least one arm in an outward direction is restricted by the arm accommodating section, and
wherein the catheter assembly is configured such that, when the outer tube is retracted with respect to the inner tube, the at least one arm projects distally from the arm accommodating section, and the at least one arm is displaced outwardly by an elastic restoring force.

4. The catheter assembly according to claim 1, further comprising a shutter member disposed in the inner tube.

5. The catheter assembly according to claim 1,
wherein the catheter assembly is configured such that, in a state in which the tip of the inner needle is positioned distal of the stopper, the stopper is contacted by the inner needle and engaged with the outer tube, whereby the outer tube is prevented from being retracted with respect to the inner tube, and
wherein the catheter assembly is configured such that, when the tip of the inner needle is positioned proximal of the stopper, the stopper is displaced inwardly and engagement of the stopper with the outer tube is released, whereby the outer tube becomes retractable with respect to the inner tube.

6. A catheter assembly comprising:
an inner needle having a sharp tip at a distal end thereof;
an inner needle hub connected to a proximal end portion of the inner needle;
a catheter through which the inner needle is inserted;
a catheter hub connected to a proximal end portion of the catheter; and
a protector that covers at least the tip of the inner needle when the inner needle is withdrawn,
wherein the protector comprises:
an inner tube that includes at least one arm that releasably engages with a proximal end of the catheter hub from an outer side of the catheter hub,
an outer tube in which the inner tube is arranged, and which is configured to be displaced in an axial direction relative to the inner tube, and
a positioning unit configured to position the inner tube at a predetermined position with respect to the outer tube,
wherein the catheter assembly is configured such that, when the inner needle is withdrawn, after the tip of the inner needle has been stored in the protector, the outer tube is retracted with respect to the inner tube thereby allowing the at least one arm to be displaced outwardly, whereby engagement between the at least one arm and the catheter hub is released, and
wherein the catheter assembly is configured such that, in a state in which the inner tube is positioned at the predetermined position with respect to the outer tube, the at least one arm is maintained in an outwardly displaced condition.

7. The catheter assembly according to claim 6, wherein the positioning unit comprises:
a first protrusion and a second protrusion, which are separated from one another in the axial direction on an outer circumferential portion of the inner tube, and
an engagement member disposed on the outer tube and which is capable of engagement with the first protrusion and the second protrusion, and
wherein the catheter assembly is configure such that, when the inner tube is positioned at the predetermined position with respect to the outer tube, the engagement member is disposed between the first protrusion and the second protrusion.

8. The catheter assembly according to claim 7,
wherein the first protrusion is disposed distal of the second protrusion, and
wherein the catheter assembly is configured such that when the outer tube is retracted with respect to the inner tube, the first protrusion and the engagement member come into abutment, whereby further movement of the outer tube with respect to the inner tube is restricted.

9. The catheter assembly according to claim 8, wherein a height of the second protrusion is smaller than a height of the first protrusion.

10. The catheter assembly according to claim 9,
wherein the inner tube further comprises a hollow inner tube main body,
wherein the at least one arm is disposed integrally on an outer side of the inner tube main body, and
wherein the outer tube comprises an arm accommodating section in which the at least one arm is accommodated.

11. The catheter assembly according to claim 10,
wherein the catheter assembly is configured such that, in a state in which the at least one arm is arranged in an interior of the arm accommodating section, displacement of the at least one arm in an outward direction is restricted by the arm accommodating section, and wherein the catheter assembly is configured such that, when the outer tube is retracted with respect to the inner tube, the at least one arm projects distally from the arm accommodating section, and the at least one arm is displaced outwardly by an elastic restoring force.

12. The catheter assembly according to claim 11, wherein the inner tube comprises:
   an insertion hole that extends in an axial direction and in which the inner needle is disposed, and
   a stopper disposed so as to face the insertion hole and which is configured to be releasably engaged with the outer tube.

13. The catheter assembly according to claim 12,
   wherein the catheter assembly is configured such that, in a state in which the tip of the inner needle is positioned distal of the stopper, the stopper is contacted by the inner needle and engaged with the outer tube, whereby the outer tube is prevented from being retracted with respect to the inner tube, and
   wherein the catheter assembly is configured such that, when the tip of the inner needle is positioned proximal of the stopper, the stopper is displaced inwardly and engagement of the stopper with the outer tube is released, whereby the outer tube becomes retractable with respect to the inner tube.

14. The catheter assembly according to claim 1, wherein the catheter hub comprises a hemostasis valve, a seal member, and a plug.

15. A catheter assembly comprising:
   an inner needle having a sharp tip at a distal end thereof;
   an inner needle hub connected to a proximal end portion of the inner needle, the inner needle hub comprising:
      a hollow hub main body configured to be gripped by a user, and
      a hollow inner needle retaining member that is configured to be fitted into a proximal end side of the hub main body and that is configured to fix the proximal end portion of the inner needle;
   a catheter through which the inner needle is inserted;
   a catheter hub connected to a proximal end portion of the catheter; and
   a protector that covers at least the tip of the inner needle when the inner needle is withdrawn,
   wherein the protector comprises:
      an inner tube that includes at least one arm that releasably engages with a proximal end of the catheter hub from an outer side of the catheter hub, and
      an outer tube in which the inner tube is arranged, and which is configured to be displaced in an axial direction relative to the inner tube,
   wherein the catheter assembly is configured such that, when the inner needle is withdrawn, after the tip of the inner needle has been stored in the protector, the outer tube is retracted with respect to the inner tube thereby allowing the at least one arm to be displaced outwardly, whereby engagement between the at least one arm and the catheter hub is released.

16. The catheter assembly according to claim 15, wherein the inner needle hub further comprises a filter which covers a proximal end side of the inner needle retaining member and is configured to block a flow of liquid but allow air to pass.

17. A catheter assembly comprising:
   an inner needle having a sharp tip at a distal end thereof;
   an inner needle hub connected to a proximal end portion of the inner needle;
   a catheter through which the inner needle is inserted;
   a catheter hub connected to a proximal end portion of the catheter; and
   a protector that covers at least the tip of the inner needle when the inner needle is withdrawn,
   wherein the protector comprises:
      an inner tube that includes at least one arm that releasably engages with a proximal end of the catheter hub from an outer side of the catheter hub,
      an outer tube in which the inner tube is arranged, and which is configured to be displaced in an axial direction relative to the inner tube, and
      a joint tube that is disposed in the inner needle hub and is axially slidable with respect to the outer tube,
   wherein the catheter assembly is configured such that, when the inner needle is withdrawn, after the tip of the inner needle has been stored in the protector, the outer tube is retracted with respect to the inner tube thereby allowing the at least one arm to be displaced outwardly, whereby engagement between the at least one arm and the catheter hub is released.

18. The catheter assembly according to claim 17, wherein, the catheter assembly is configured such that, when the inner needle hub is retracted by a first predetermined amount, a step, which is disposed on the distal end side of the inner needle hub, engages with an outer side hook on a proximal end side of the joint tube, causing the joint tube to also retract.

19. The catheter assembly according to claim 18, wherein the catheter assembly is configured such that, when the inner needle hub is retracted by a second predetermined amount, an inner side hook on the distal end side of the joint tube engages with an outer side hook on the proximal end side of the outer tube causing the outer tube to also retract.

* * * * *